United States Patent [19]
Stambaugh

[11] Patent Number: 6,136,011
[45] Date of Patent: Oct. 24, 2000

[54] STENT DELIVERY SYSTEM AND METHOD OF USE

[75] Inventor: James W. Stambaugh, Castro Valley, Calif.

[73] Assignee: Advanced Cardiovascular Systems, Inc., Santa Clara, Calif.

[21] Appl. No.: 09/114,850

[22] Filed: Jul. 14, 1998

[51] Int. Cl.[7] .................................................. A61B 17/22
[52] U.S. Cl. .......................... 606/159; 606/108; 606/194; 604/101
[58] Field of Search ..................................... 606/159, 108, 606/191, 192, 193, 194, 195, 196, 197, 198; 604/101

[56] References Cited

U.S. PATENT DOCUMENTS

| | | |
|---|---|---|
| 3,868,956 | 3/1975 | Alfidi et al. . |
| 4,323,071 | 4/1982 | Simpson et al. . |
| 4,503,569 | 3/1985 | Dotter . |
| 4,512,338 | 4/1985 | Balko et al. . |
| 4,516,972 | 5/1985 | Samson . |
| 4,553,545 | 11/1985 | Maass et al. . |
| 4,560,374 | 12/1985 | Hammerslag . |
| 4,616,652 | 10/1986 | Simpson . |
| 4,655,771 | 4/1987 | Wallsten . |
| 4,665,918 | 5/1987 | Garza et al. . |
| 4,733,665 | 3/1988 | Palmaz . |
| 4,748,982 | 6/1988 | Horzewski et al. . |
| 4,760,849 | 8/1988 | Kropf . |
| 4,762,128 | 8/1988 | Rosenbluth . |
| 4,768,507 | 9/1988 | Fischell . |
| 4,771,777 | 9/1988 | Horzewski et al. . |
| 4,795,458 | 1/1989 | Regan . |

(List continued on next page.)

FOREIGN PATENT DOCUMENTS

| | | |
|---|---|---|
| 8901798 | 3/1989 | European Pat. Off. . |
| 8908433 | 9/1989 | European Pat. Off. . |
| 0408245 | 1/1991 | European Pat. Off. . |
| 36 40 745 | 6/1987 | Germany . |
| 3823060 | 1/1989 | Germany . |

OTHER PUBLICATIONS

Finci, Leo, M.D., et al., Percutaneous Transluminal Coronary Angioplasty of a Bifurcation Narrowing Using the Kissing Wire Monorail Balloon Technique, *The American Journal of Cardiology*, Apr. 1987.

Bonzel, T., et al., The Sliding Rail system (Monorail): Description of a New Technique for Intravascular Instrumentation and its Application to Coronary Angioplasty, *Kardiologie*, Supplement 6, pp. 119–122 (1987).

van der Giessen, Willem J., et al., Coronary Stenting With a New, Radiopaque Balloon–Expandable Endoprosthesis is Pigs, *Circulation*, vol. 83, No. 5, pp. 93–149, May 1991.

Kaltenbach, M., Prof. Dr., Abstracts, *Zeitschrift für Kardiologie*, Apr. 3, 1991 (German only).

Strupp, G. et al., Clinical and Angiographic Short and Medium Term Results After Coronary Stenting, *Zietschrift für Kardiologie*, Sep. 9, 1992 (German with English language summary).

Harrington, John C., The Palmaz–Schotz Stent, *Handbook of Cardiovascular Interventions/Vascular Interventions*, pp. 563–572 (Undated).

*Primary Examiner*—Michael Buiz
*Assistant Examiner*—Lien Ngo
*Attorney, Agent, or Firm*—Fulwider Patton Lee & Utecht, LLP

[57] ABSTRACT

A stent deployment system and method wherein a two balloon catheter is used to expand the stent within a body lumen. The balloons are concentrically arranged about a dual lumen catheter wherein the inner balloon is smaller than the outer balloon. By first inflating the smaller balloon to expand only the center section of the stent, the stent undergoes substantially all of its longitudinal contraction before the ends make contact with the lumen tissue upon inflation of the larger outer balloon.

9 Claims, 2 Drawing Sheets

U.S. PATENT DOCUMENTS

| | | |
|---|---|---|
| 4,800,882 | 1/1989 | Gianturco . |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,887,997 | 12/1989 | Wiktor . |
| 4,892,539 | 1/1990 | Koch . |
| 4,907,336 | 3/1990 | Gianturco . |
| 4,913,141 | 4/1990 | Hillstead . |
| 4,921,479 | 5/1990 | Grayzel . |
| 4,923,464 | 5/1990 | DiPisa, Jr. . |
| 4,950,227 | 8/1990 | Savin et al. . |
| 4,969,458 | 11/1990 | Wiktor . |
| 4,988,356 | 1/1991 | Crittenden et al. . |
| 5,019,090 | 5/1991 | Pinchuk . |
| 5,034,001 | 7/1991 | Garrison et al. . |
| 5,061,273 | 10/1991 | Yock . |
| 5,133,732 | 7/1992 | Wiktor . |
| 5,135,536 | 8/1992 | Hillstead . |
| 5,161,547 | 11/1992 | Tower . |
| 5,163,951 | 11/1992 | Pinchuk et al. . |
| 5,163,952 | 11/1992 | Froix . |
| 5,163,958 | 11/1992 | Pinchuk . |
| 5,171,262 | 12/1992 | MacGregor . |
| 5,183,085 | 2/1993 | Timmermans . |
| 5,192,297 | 3/1993 | Hull . |
| 5,192,307 | 3/1993 | Wall . |
| 5,192,311 | 3/1993 | King et al. . |
| 5,195,984 | 3/1993 | Schatz . |
| 5,197,978 | 3/1993 | Hess . |
| 5,258,020 | 11/1993 | Froix . |
| 5,263,964 | 11/1993 | Purdy . |
| 5,282,823 | 2/1994 | Schwartz et al. . |
| 5,282,824 | 2/1994 | Gianturco . |
| 5,290,295 | 3/1994 | Querals et al. . |
| 5,368,566 | 11/1994 | Crocker . |
| 5,372,600 | 12/1994 | Beyar et al. . |
| 5,378,239 | 1/1995 | Termin et al. . |
| 5,403,280 | 4/1995 | Wang ...................................... 606/194 |
| 5,405,378 | 4/1995 | Strecker . |
| 5,409,495 | 4/1995 | Osborn ................................... 606/194 |
| 5,456,694 | 10/1995 | Marin et al. . |
| 5,476,476 | 12/1995 | Hillstead . |
| 5,484,449 | 1/1996 | Amundson et al. . |
| 5,507,768 | 4/1996 | Lau et al. . |
| 5,653,689 | 8/1997 | Buelna et al. . |
| 5,707,358 | 1/1998 | Wright ................................... 604/101 |
| 5,725,535 | 3/1998 | Hegde et al. . |

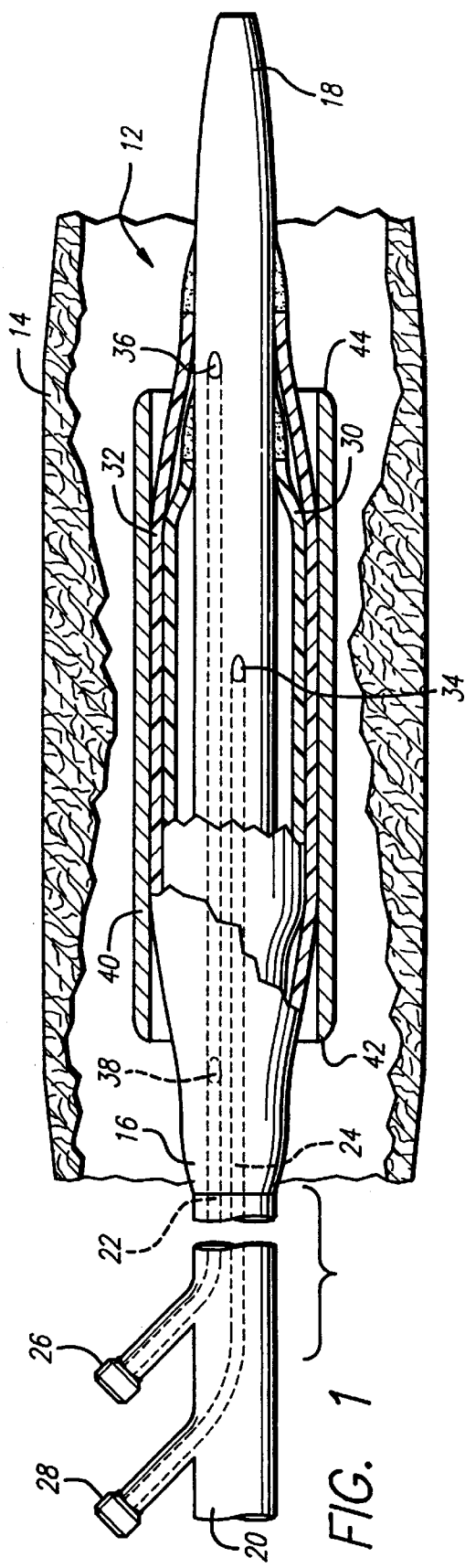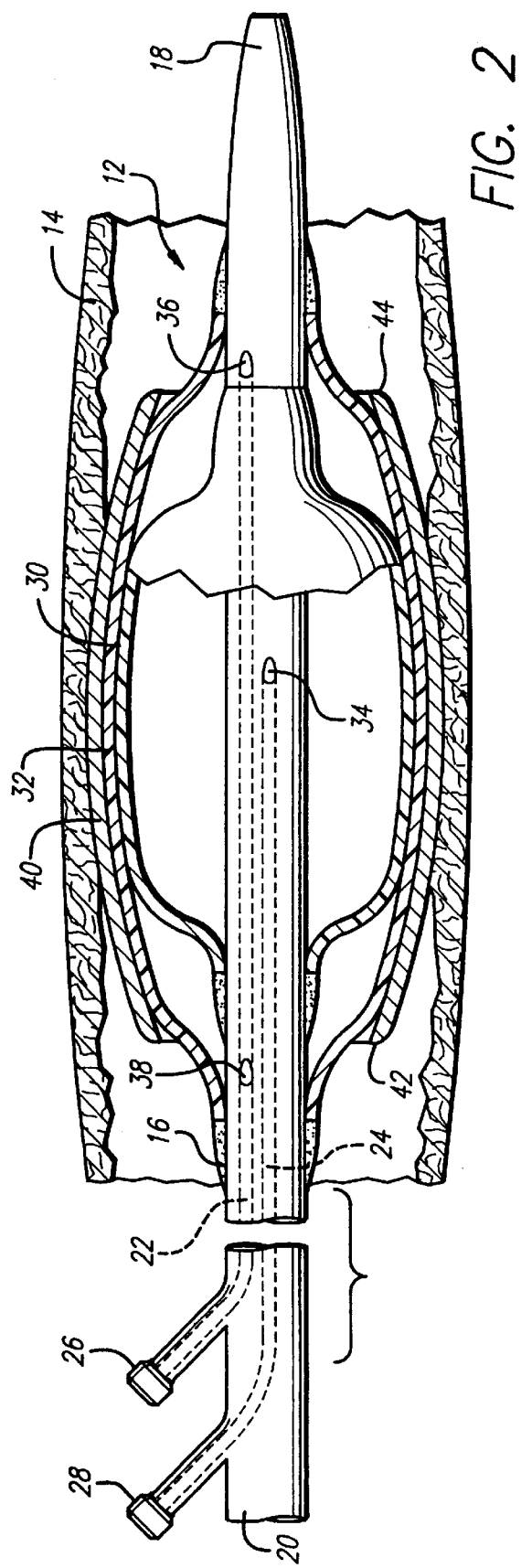

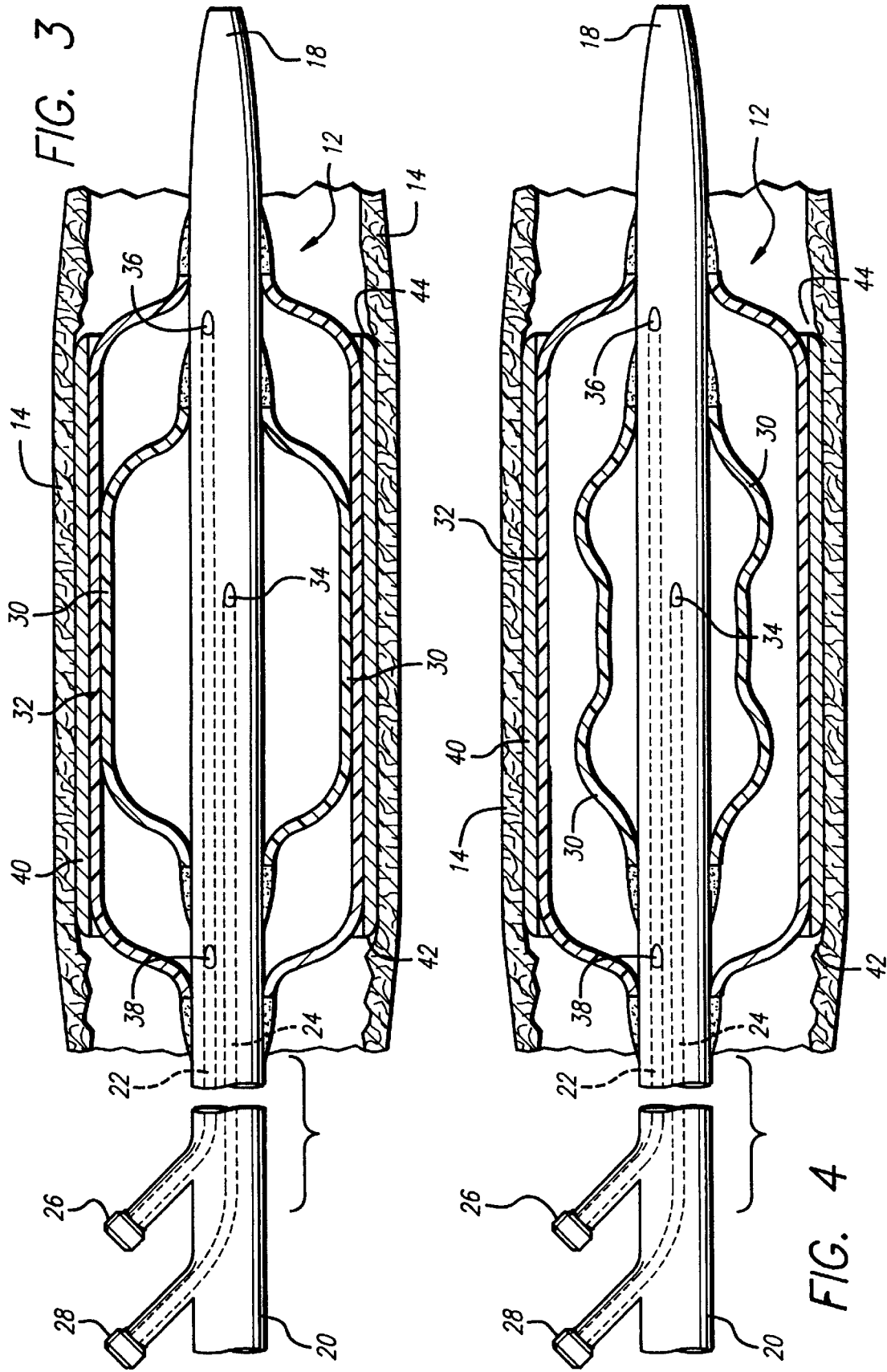

STENT DELIVERY SYSTEM AND METHOD OF USE

BACKGROUND OF THE INVENTION

The present invention generally relates to balloon catheters for implanting stents within a body lumen. More particularly, the invention pertains to improvements to such catheters in order to more effectively and reliably achieve a uniform expansion of such stents while minimizing trauma to the vessel wall.

Stents or expandable grafts are implanted in a variety of body lumens in order to prevent collapse and thereby maintain the patency of such lumens. In the case of angioplasty applications, stents may also be implanted to prevent restenosis and thereby similarly maintain patency in the affected blood vessel. The stent is introduced into the body in a collapsed state to facilitate its transport to the deployment site where it is subsequently expanded. One approach for achieving expansion requires the stent in its contracted state to be fitted about an inflatable balloon disposed near the distal end of a catheter. The entire assembly is advanced through the vasculature and maneuvered into the desired position adjacent the section of lumen in need of support. Once in position, the balloon is inflated causing the stent to expand and engage the lumen walls. Various stent configurations and mechanisms have been devised to lock the stent into its expanded state in order to provide the requisite radial support to the lumen. Once the stent is fully expanded, the balloon is deflated and the catheter removed to leave the stent in place. Some stents are designed to permanently remain implanted while others are formed of materials that eventually become absorbed by the body.

The effectiveness of a stent can be diminished if it is not uniformly implanted within the body lumen. Stents expanded by the inflation of a balloon have a tendency to undergo a disproportionate rate and amount of radial expansion at their proximal and distal ends due to the typical drop off in hoop strength encountered near the ends of the structure. Thus the balloon expands along the path of least resistance in a "dog bone" pattern which is similarly imparted to the stent. Such non-uniformity in the implanted stent may be problematic in that the desired flow diameter of the stent may not be achievable without forcing the stent ends deep into the lumen tissue. In the case of arterial applications, the non-uniformity of surfaces encountered by blood flow may cause turbulence which in turn may lead to thrombosis.

A further disadvantage inherent in many stent configurations currently in use is that the structure undergoes longitudinal contraction as it is expanded radially. This characteristic, in conjunction with the tendency of the stent ends to expand first, has the potential for inflicting trauma on the lumen in which the stent is being deployed. Because the initial expansion of the stent ends may cause such ends to project into the lumen tissue, the subsequent radial expansion and hence longitudinal contraction of the center section would cause such ends to be pulled across the tissue. The rubbing or scraping of the stent against the tissue could cause injury.

This problem has been previously addressed in a number of ways including for example, the use of shape defining sleeves that are fitted about the balloon. It is the intent of such system to match the radial force profile generated by the balloon to the hoop strength of the stent and thereby achieve a constant rate of expansion over the length of the stent.

Alternatively, multiple balloon systems have been employed in an effort to control the expansion of the stent. In one system, "control" balloons are positioned proximally and distally to a centrally disposed expansion balloon. The two control balloons check axial growth of the expansion balloon and hence prevent axially displaced lateral loads to be placed on the stent. As a further alternative, the stent is positioned over multiple balloons of varied compliance arranged in series along the catheter. By sequencing the inflation of the balloons such that the central balloon is inflated first, a more uniform implantation of the stent is achieved.

Nonetheless, those concerned with the design, development and use of stent implantation systems recognize the desirability of further improvements in terms of performance efficiency, reliability and reductions in the cost of manufacture.

SUMMARY OF THE INVENTION

The present invention overcomes the shortcomings inherent in heretofore known deployment devices and techniques for balloon expandable stents. More specifically, the present invention provides for the uniform deployment of such stents while obviating the trauma that the stent's ends can inflict on the lumen walls. This is achieved more effectively, more reliably and with a device less costly to manufacture than was previously possible.

The invention provides for the center section to be expanded before the stent's ends are expanded using a two balloon system. As a result, the stent structure undergoes substantially its entire longitudinal contraction before the ends make contact with the vessel walls. The potential for the ends to be rubbed or scraped across the lumen tissue and cause injury is thereby effectively obviated. Such advantage is achieved with the use of two independently inflatable balloons concentrically fitted about a catheter. One balloon is positioned within the other wherein the outer balloon corresponds to the length of the stent while the inner balloon is substantially shorter. The inflated diameter of the outer balloon is approximately equal to the inflated diameter of the inner balloon or slightly smaller to accommodate the diminished hoop strength of the ends of the stent.

The deployment device of the present invention allows the stent to be initially expanded by the inner balloon, which by virtue of its smaller length causes only the center section of the stent to be radially expanded. The stent undergoes the majority of its longitudinal contraction during such initial expansion and only after such longitudinal contraction has been realized is the longer, outer balloon inflated to cause the stent's ends to expand and match the diameter of the center section. Trauma to the vessel walls by the stent ends is thereby effectively avoided. The configuration of some stents and the commensurate hoop strength variations along the length of such stents may require the outer balloon to have a slightly smaller inflated diameter than the inner balloon to avoid any "dog boning".

The use of only two balloons rather than the three balloons employed in some previously known in systems not only enhances reliability but reduces manufacturing cost. The fact that the use of two balloons requires a lesser number of surfaces to be bonded and sealed to the catheter surface also enhances the reliability of the device. Moreover, in the event of the failure of the inner balloon, any expansion fluid that is lost is contained by the outer balloon. Moreover, the outer balloon can effect sufficient expansion of the stent to allow the catheter to be disengaged therefrom and withdrawn.

These and other features and advantages of the present invention will become apparent from the following detailed description of a preferred embodiment which, taken in conjunction with the accompanying drawings, illustrates by way of example the principles of the invention.

BRIEF DESCRIPTION OF THE DRAWINGS

FIG. 1 is an enlarged, sectioned and cross-sectional view of the stent delivery system of the present invention prior to deployment of the stent;

FIG. 2 is an enlarged, sectioned and cross-sectional view of the stent delivery system after inflation of the inner balloon;

FIG. 3 is an enlarged, sectioned and cross-sectional view of the stent delivery system after inflation of the outer balloon; and FIG. 4 is an enlarged, section and cross-sectional view of the stent delivery system with the inner balloon deflated so that the outer balloon can be fully inflated.

DETAILED DESCRIPTION OF THE PREFERRED EMBODIMENTS

The figures generally illustrate the stent delivery system of the present invention before, during and after deployment of the stent. Upon deployment, the stent serves to maintain the patency of the vessel in which it is positioned either by physically supporting the vessel wall or, in the case of some cardiovascular applications for example, by preventing restenosis.

FIG. 1 illustrates the system 12 in its pre-deployed pre-implanted state upon having been advanced to the deployment site within a body lumen 14. The system is introduced into the body in the conventional manner and may be advanced into position via a guide wire using conventional over-the-wire or rapid-exchange catheter techniques. Details of representative stents can be found in U.S. Pat. Nos. 5,421,955 (Lau et al.); 5,514,154 (Lau et al.); 5,603,721 (Lau et al.); and 5,569,295 (Lam), which are incorporated herein in their entirety by reference thereto. Details regarding balloon angioplasty catheters for use in performing angioplasty procedures, or that can be adapted to deliver intravascular stents are found in U.S. Pat. Nos. 4,771,777 (Horzewski et al.); 5,501,227 (Yock); 5,350,395 (Yock); 5,451,233 (Yock); 5,300,085 (Yock); 5,496,346 (Horzewski et al.); 5,061,273 (Yock); 5,040,548 (Yock); 4,748,982 (Horzewski et al.); 5,626,600 (Horzewski et al.); and 4,323,071 (Simpson et al.), which are incorporated herein in their entirety by reference thereto.

The device includes a catheter 16 having a distal end 18 and a proximal end 20 wherein such catheter has at least two inflation lumens 22, 24 formed therein. Each inflation lumen is in fluid communication with an inflation port 26,28 located near to the proximal end of the catheter.

Two inflatable balloons are fitted about the catheter near its distal end and are positioned such that the relatively shorter inner balloon 30 is wholly contained within the relatively larger outer balloon 32. The inner balloon is in fluid communication with lumen 24 via lumen port 34 while the outer balloon is in fluid communication with lumen 22 via lumen port 36 and optionally lumen port 38. The inflated diameters of the balloons are approximately equal or optionally, the outer balloon may have a slightly smaller or larger inflated diameter than the inner balloon. The length of the inner balloon preferably is approximately 70% that of the outer balloon, but preferably can be in the range of between 50% to 90% of the length of the outer balloon.

Fitted about the exterior surface of the outer balloon is the stent 40 that is to be deployed. The length of the outer balloon is selected so as to substantially conform to the length of the stent.

The balloons and catheter may be formed of polyethylene or other suitable materials well known in the art and the balloons are preferably bonded to the catheter as is also well known in the art.

In use, the catheter 16 with its balloons 30, 32 in their deflated state and supporting the stent 40 thereabout in its collapsed state is introduced into the body lumen 14 and advanced therethrough to the deployment site. Once in position, the inner balloon 30 is inflated via inflation port 28 to expand the center section of the stent 40 as is shown in FIG. 2. Such radial expansion causes the middle of the stent to expand radially outwardly and simultaneously contract longitudinally. However, because the inner balloon does not engage the ends 42, 44 of the stent, the ends do not expand substantially and remain distanced from the lumen wall. Trauma to the lumen wall that would otherwise be inflicted by the ends is avoided as the stent undergoes longitudinal contraction. Once the inner balloon is filly inflated, the outer balloon 32 is inflated via inflation port 26 as is shown in FIG. 3. In the event two lumen ports 36, 38 are formed in the inflation lumen, there is no need to first deflate the inner balloon 30. In the event only a single lumen port is employed, it is necessary to first reduce the pressure within the inner balloon in order to provide a fluid pathway for the entire interior of the outer balloon into fluid communication with such single port, as shown in FIG. 4. As the outer balloon expands, the ends 42, 44 of the stent are expanded to their fully deployed state to impart a uniformly expanded profile to the stent. Deflation of both balloons 30, 32 leaves the stent 40 in place against the lumen walls and frees the catheter 16 for retraction.

The balloons are preferably inflated by radiopaque fluid to facilitate monitoring of its position and shape by fluoroscopic means. The details and mechanics of balloon inflation vary according to the specific design of the catheter and are well known in the art. Similarly, different stent configurations may require the relative sizes of the balloons and the pressures to which they are inflated to be adjusted accordingly.

While a particular form of the invention has been illustrated and described, it will also be apparent to those skilled in the art that various modifications can be made without departing from the spirit and scope of the invention. The invention is not limited to the implantation of the stent in any particular body lumen nor to any particular configuration or size of the stent. Accordingly, it is not intended that the invention be limited except by the appended claims.

What is claimed is:

1. A stent delivery catheter assembly for an expandable stent, comprising:

a multi-lumen catheter dimensioned to be advanceable through vasculature to a deployment site;

an inner inflation balloon, having a first preselected inflated length and diameter disposed about said catheter and in fluid communication with a first lumen formed in said catheter;

an outer inflation balloon, having a second preselected inflated length and diameter disposed about said catheter, wherein the inflated length of said outer balloon is greater than the inflated length of said inner balloon, wherein the inflated diameter of said outer balloon is no greater than said inflated diameter of said inner balloon and wherein said outer balloon is positioned to centrally contain said inner balloon; and an expandable stent mounted on the outer inflation balloon.

2. The apparatus of claim 1, wherein said inner balloon is about 70% as long as said outer balloon.

3. The apparatus of claim 1, wherein said inner balloon is in the range of 50% to 90% as long as said outer balloon.

4. The apparatus of claim 1, wherein the inflated diameter of said outer balloon is less than the inflated diameter of said inner balloon.

5. The apparatus of claim 1, wherein said inflated length of said outer balloon is substantially equal to that of a stent to be deployed.

6. The apparatus of claim 1, wherein said balloons are bonded to said catheter.

7. A method of deploying an expandable stent within a body lumen, comprising the steps of:

crimping a stent on to an outer inflation balloon containing a smaller centrally located, inner inflation balloon which are disposed about a catheter;

advancing said stent and balloon carrying catheter to a deployment site;

inflating said inner balloon to partially expand said stent; and inflating said outer balloon to fully expand said stent.

8. The method of claim 7, further comprising the step of deflating said inner balloon prior to inflating said outer balloon.

9. The method of claim 7, wherein said inner balloon remains inflated as said outer balloon is inflated.

* * * * *

UNITED STATES PATENT AND TRADEMARK OFFICE
CERTIFICATE OF CORRECTION

PATENT NO. : 6,136,011
DATED : October 24, 2000
INVENTOR(S) : James W. Stambaugh Page 1 of 1

It is certified that error appears in the above-identified patent and that said Letters Patent is hereby corrected as shown below:

Column 4, claim 1,
Line 64, after "catheter," add -- and in fluid communication with a second lumen in said catheter --.

Column 6, claim 7,
Line 2, after "balloon", add -- said balloons being --.
Line 3, delete "which are", and after "catheter", add -- comprising a first inflation lumen in communication with said outer balloon and a second inflation lumen in fluid communication with said inner balloon; --.
Line 6, delete "inflating", and replace with -- providing pressurized medium through said second inflation lumen to inflate --.
Line 8, delete "inflating", and replace with -- providing pressurized medium through said first inflation lumen to inflate --.

Signed and Sealed this

Fifth Day of March, 2002

*Attest:*

JAMES E. ROGAN
*Attesting Officer*     *Director of the United States Patent and Trademark Office*